United States Patent [19]

Chaney

[11] Patent Number: 5,061,234
[45] Date of Patent: Oct. 29, 1991

[54] MAGNETIC NEURAL STIMULATOR FOR NEUROPHYSIOLOGY

[75] Inventor: Richard A. Chaney, Nashua, N.H. 03062

[73] Assignee: Corteks, Inc., Chappaqua, N.Y.

[21] Appl. No.: 411,932

[22] Filed: Sep. 25, 1989

[51] Int. Cl.⁵ .............................................. A61N 2/04
[52] U.S. Cl. ...................................................... 600/14
[58] Field of Search .................................. 600/13–15; 361/156

[56] References Cited

U.S. PATENT DOCUMENTS

| | | | |
|---|---|---|---|
| 3,986,493 | 10/1976 | Hendren | 600/12 |
| 4,551,781 | 11/1985 | Bykerk | 361/143 |
| 4,561,426 | 12/1985 | Stewart | 128/1.5 |
| 4,574,809 | 3/1986 | Talish et al. | 128/419 F |
| 4,607,311 | 8/1986 | Brown et al. | 361/155 |
| 4,778,971 | 10/1988 | Sakimoto et al. | 219/10.43 |

FOREIGN PATENT DOCUMENTS 1113156 11/1981 Canada ................................. 600/14

OTHER PUBLICATIONS

Maass et al., "Contactless Nerve Stimulation and Signal Detection by Inductive Transducer", *IEEE Transactions on Magnetics*, vol. Mag–6, No. 2, pp. 322–326, (Jun. 1970).
Hallgren et al., "Contactless Nerve Stimulating Transducer", *IEEE Transaction on Biomedical Engineering*, pp. 316–317, (Jul. 1972).
Oberg, "Magnetic Stimulation of Nerve Tissue", *Medical and Biological Engineering*, pp. 55–64, (Jan. 1973).
Hallgren, "Inductive Neural Stimulator", *IEEE Transactions on Biomedical Engineering*, pp. 470–472, (Nov. 1973).
Ueno et al., "Capacitive Stimulatory Effect in Magnetic Stimulation of Nerve Tissue", *IEEE Transactions on Magnetics*, vol. Mag–14, No. 5, pp. 958–960, (Sep. 1978).
Polson et al., "Stimulation of Nerve Trunks with Time–Varying Magnetic Fields", *Medical and Biological Engineering and Computing*, pp. 243–244, (Mar. 1982).
Freeston et al., "Nerve Stimulation Using Magnetic Fields", *IEEE Frontiers of Engineering and Computing in Health Care*, pp. 557–561, (1984).
McRobbie, "Design and Instrumentation of Magnetic Nerve Stimulator", *The Institute of Physics*, pp. 74–78, (1985).
Young et al., "Clinical Neurophysiology of Conduction in Central Motor Pathways", *Annals of Neurology*, vol. 18, No. 5, pp. 606–609, (Nov. 1985).
Hess et al., "Magnetic Brain Stimulation: Central Motor Conduction Studies in Multiple Sclerosis", *Annals of Neurology*, vol. 22, No. 6, pp. 744–752, (Dec. 1987).
Mills et al., "Magnetic and Electrical Transcranial Brain Stimulation: Physiological Mechanisms and Clinical Application", *Neurosurgery*, vol. 20, No. 1, pp. 164–168, (1987).
Barker et al., "Magnetic Stimulation of the Human Brain and Peripheral Nervous System: An Introduction (List continued on next page.)

Primary Examiner—William E. Kamm
Assistant Examiner—Kevin Pontius
Attorney, Agent, or Firm—Pennie & Edmonds

[57] ABSTRACT

A magnetic neural stimulator is disclosed for the stimulation of biological tissue. The stimulator includes an inductive stimulation coil, an energy storage capacitor, a firing device and a charging circuit. The energy storage capacitor is charged by the charging circuit to a voltage level which is greater than the voltage level supplied to the charging circuit. The energy storage capacitor is partially discharged into the stimulation coil thereby producing a magnetic pulse. The charging and discharging of the capacitor is continuously performed so as to produce a plurality of high frequency magnetic pulses. The stimulation coil and the energy storage capacitor operate in a resonant manner under a control circuit which performs timing and gating functions.

8 Claims, 7 Drawing Sheets

OTHER PUBLICATIONS and the Results of an Initial Clinical Evaluation", *Neurosurgery*, vol. 20, No. 1, pp. 100–109, (1987).

Macabee et al., "Intracranial Stimulation of Facial Nerve in Humans with the Magnetic Coil", *Electroencephalography and Clinical Neurophysiology*, vol. 70, pp. 350–354, (1988).

Schriefer et al., "Evaluation of Proximal Facial Nerve Conduction by Transcranial Magnetic Stimulator", *Journal of Neurology, Neurosurgery, and Psychiatry*, vol. 51, pp. 60–66, (1988).

Tsuji et al., "Somatosensory Potentials Evoked by Magnetic Stimulation of Lumbar Roots, Cauda Equina and Leg Nerves", Annals of Neurology, vol. 24, No. 4, pp. 568–573, (1988).

Claus et al., "Central Motor Conduction in Degenerative Ataxic Disorders: A Magnetic Stimulation Study", *Journal of Neurology, Neurosurgery and Psychiatry*, 51, pp. 790–795, (1988).

MAGNETIC NEURAL STIMULATOR FOR NEUROPHYSIOLOGY

BACKGROUND OF THE INVENTION

The present invention relates generally to magnetic stimulation and more particularly to high-speed magnetic stimulation of biological tissue.

For some time, electrical or magnetic stimulation devices have been used to stimulate biological tissue.

Electric stimulation of biological tissue is wellknown and generally involves the use of a plurality of electrodes strategically placed on the tissue of a subject (human or animal). Electric pulses are subsequently generated and applied to the electrodes. The tissue in an area separating the electrodes is thus stimulated by the passage of current therethrough.

Magnetic stimulation of biological tissue is a much more recent development. Magnetic stimulation involves the application of a magnetic field to biological tissue. A magnetic transducer such as a wire wound coil is employed to generate the magnetic field. The coil may be contactless and operate a predetermined distance away from the subject. Alternatively, the coil may contact or may be implanted in the subject.

Magnetic stimulation offers many significant advantages over electrical stimulation. Magnetic stimulation eliminates the need for direct physical electrical contact to the subject and thus removes problems associated with high skin electrical resistance, damage to tissue due to high current flow and the like. Additionally, the subject is exposed to less risk since hazards arising from electrical shock due to malfunctioning equipment are reduced, if not eliminated.

Potential applications of magnetic stimulation also include the stimulation of both the central and peripheral nervous systems. Specifically, magnetic stimulation followed by recordal of the corresponding motor evoked potentials (MEPs) is believed to be a promising application of magnetic neural stimulation. MEPs have been recorded over spinal cord, peripheral nerve and muscle following transcranial electrical stimulation. These MEPs have been demonstrated to accurately reflect the functional integrity of efferent spinal motor pathways of rats and cats subjected to mechanical trauma, compression and ischemia, and also have been well correlated with the degree of clinical recovery. These results suggest major clinical applications for MEPs in evaluation of efferent motor pathways as well as in intraoperative monitoring. Conventional neurophysiological techniques do not permit such examination of central motor pathways.

With respect to diagnostic evaluation of efferent motor pathways, MEP abnormalities have been demonstrated in patients with multiple sclerosis, compressive and radiation induced myelopathies, and hereditary spastic paraparesis. In some cases subclinical dysfunction was detected.

Further, intraoperative monitoring of efferent motor pathways is likely to achieve major importance supplementing somatosensory evoked potential (SEP) monitoring during neurosurgery. SEPs, which monitor principally dorsal cord function, do not adequately predict the integrity of the descending motor pathways. Successful use of MEP monitoring has been reported in a large series of neurosurgical procedures, where monitoring results correlated well with clinical outcome. Although at present transpinal cord stimulation is not known to have been reported, this may also be possible.

Magnetic neural stimulation is also likely to be a useful research tool for brain physiology. Using electrical stimulation, MEP to cerebellar stimulation has been demonstrated and used to study interactions of pyramidal and extra-pyramidal motor systems. MEPs have also been used to study the function of callosal pathways. It is likely that many further research applications for the study of brain physiology will emerge. Magnetic stimulation of the brain provides instrumental, noninvasive access to brain function, with the possibility of modification of that function.

Magnetic neural stimulation offers several potential advantages over conventional electrical stimulation. Magnetic stimulation is painless. Transcutaneous electrical stimulation produces the greatest current density in the most superficial skin layers, the skin layers most sensitive to pain. In contrast, lines of flux produced by magnetic stimulation penetrate the skin essentially unaltered, making it possible to stimulate nerves without exciting overlying cutaneous pain fibers, which have a higher threshold for stimulation.

The painless nature of magnetic stimulation will likely prove a major practical advantage in performing peripheral nerve and SEP studies on children. Moreover, the electrophysiological examination of deeper lying and proximal peripheral nerve, which is inaccessible to study by conventional electrical stimulation because of the painful and potentially damaging currents required to excite deep lying tissue, appears to be feasible using magnetic stimulation.

Rapid electrical stimulation of peripheral nerve is sufficiently painful so that this technique cannot be employed on conscious patients. Fortunately, magnetic stimulation at similarly high rates of stimulation is painless.

Magnetic stimulation produces substantially less stimulus artifact than electrical stimulation. This will facilitate SEP recordings in settings where the time interval between stimulus and response is very short, such as recordings in infants and small children, trigeminal nerve SEPs, and blink reflex recordings.

Magnetic stimulation may make transcutaneous clinical evaluation of small, unmyelinated nerve pathways possible. Although potentially useful techniques for small and selective fiber stimulation have been proposed, these techniques have not been successfully used transcutaneously in a clinical setting, most likely due to the high currents that would be required, as well as the effect of skin and nerve upon the pulse shape. Since magnetic fields are not substantially altered by the skin and nerve sheath, it may be possible to use a magnetic stimulator capable of delivering a shaped magnetic pulse to selectively stimulate smaller myelinated and unmyelinated fibers.

Unfortunately, practical use of magnetic neural stimulation has been limited by the inability of currently available magnetic neural stimulators to selectively stimulate a limited area of neural tissue, especially cerebral, spinal or peripheral neural tissue. Presently available stimulators employ large stimulating coils which are incapable of focusing and limiting the lateral spread of the magnetic field. Additionally, the ability to selectively stimulate more discrete areas of tissue such as the brain will be important in gaining an understanding of the physiology of magnetic nerve stimulation and may also enhance its ultimate clinical utility. Furthermore, many peripheral neurophysiological tests involve determination of nerve conduction velocity, and hence require accurate knowledge of precisely where nerve stimulation occurred.

Present devices also cannot stimulate at rates over about 1 Hz. As a result, clinical MEP testing and monitoring is presently restricted for practical purposes to recording of electromyogram (EMG) activity only. Although the sensitivity of clinical studies would likely be enhanced by recording neural responses over spinal cord and peripheral nerve, such studies would require signal averaging, which is impractical at low stimulation rates.

Present magnetic neural stimulators are also unable to operate at the speed necessary for SEP testing since averaging of response to a prohibitively large number of stimuli is required. Thus, magnetic peripheral nerve stimulation, although pain-free, is also not practical for SEP testing using presently available devices. Present devices are also unable to selectively stimulate a limited area of neural tissue.

SUMMARY OF THE INVENTION

We have devised a high speed, compact, cost effective magnetic neural stimulator capable of selectively stimulating small regions of tissue. Such stimulation can result in the sustained contraction of biological tissue. Broadly, the stimulator comprises a charging power supply, stimulation means, energy storage means, firing means, a resonant charging circuit and control circuit means.

The charging power supply supplies the energy to initially produce the magnetic pulses as well as the energy to compensate for the energy lost as heat during steady-state operation. The output voltage of this supply may be adjusted to give different stimulus intensities.

The stimulation means is preferably an inductor in the form of a wire wound coil and is located within a hand held stimulation probe. Magnetic pulse shaping material is provided in close proximity to the inductor. The inductor is connected to the system through cables and high current connectors. The inductor and the magnetic pulse shaping material are configured to enable magnetic pulse shaping which facilitates stimulation of selective regions of tissue, especially nerve fibers.

The energy storage means is powered by the charging power supply and stores the energy employed by the stimulation coil to produce magnetic pulses. Illustratively, the energy storage means is implemented as a group or bank of capacitors connected in parallel.

The resonant charging circuit operates in conjunction with the stimulation coil and energy storage means to generate high frequency magnetic pulses by transferring energy from the energy storage means into a magnetic field and back into the energy storage means in a resonant fashion. The resonant charging circuit, in combination with the control circuit and firing means, restores energy lost through the stimulation coil and other components, wires, etc. by extracting the amount of lost energy from the power supply and supplying it to the energy storage means. Viewed another way, the resonant charging circuit, in combination with the control circuit and firing means, causes the energy storage means to only partially discharge through the inductor of the stimulation coil. The resonant charging circuit may be in the form of a serially connected inductor and diode connected at one end to the charging power supply and at another end to the stimulation probe and the energy storage means. In this preferred embodiment, the inductor and the diode supply the current path to charge the energy storage means.

The control circuit means includes a transformer isolated gate driver and operates in conjunction with a firing means such as a silicon-controlled rectifier (SCR), linear amplifier or plasma switch. The gate driver is powered by a low voltage power supply. The firing means is serially connected with the stimulation probe across the energy storage means and serves as a high current switch to fire the inductor of the stimulation probe under control of the gate driver. Depending on the configuration and firing scheme of the control circuit, as well as the type of firing means, unipolar magnetic pulses as well as magnetic pulses of alternating polarity may be produced. The control circuit is responsive to the charge in the energy storage means and, like the resonant charging circuit, is instrumental in restoring lost energy by extracting the amount of energy lost from the power supply and supplying it to the energy storage means.

Advantageously, use of the resonant charging circuit in conjunction with the inductor of the hand held stimulation probe eliminates the need for a high voltage power supply. As will become apparent, the peak voltage across the capacitor bank during normal operation of the neural stimulator is significantly greater than the peak voltage of the charging power supply. As will be appreciated, each firing of the inductor in the stimulation probe will not entirely discharge the voltage across the capacitor bank, thus enabling rapid firing of the probe and sustained generation of high frequency magnetic pulses.

The neural stimulator of the present invention permits restriction of stimulation to limited regions of tissue. Additionally, the neural stimulator permits stimulation at rates up to 400 Hz and beyond depending on the available power supply and coil cooling.

The stimulator may be used in a wide variety of applications. For example, clinical applications include diagnostic and intraoperative real-time evaluation of efferent pathways, as well as allowing pain-free peripheral nerve stimulation for standard afferent pathway and peripheral nerve testing. Research applications include studies of the physiological effects of focused cortical, cerebellar, and spinal cord stimulation, as well as in vivo selective fiber stimulation.

Advantageously, magnetic neural stimulation renders the peripheral proximal nervous system, spinal cord and central motor pathways accessible to non-invasive, cost effective neurophysiological testing, and permits monitoring in critical care settings.

Accordingly, it is a principal object of the present invention to provide new and improved magnetic stimulation of biological tissue.

It is also an object of the invention to provide a magnetic stimulator including a resonant stimulator circuit to enable generation of magnetic pulses of increased frequency.

It is a further object of the invention to provide a magnetic stimulator configured to selectively stimulate small regions of biological tissue.

It is another object of the present invention to eliminate the need for a high voltage power supply in a magnetic neural stimulator.

BRIEF DESCRIPTION OF THE DRAWINGS

These and other objects, features and advantages of the invention will be more readily apparent from the following description of the invention in which.

DETAILED DESCRIPTION OF THE PREFERRED EMBODIMENT

Figure 1:
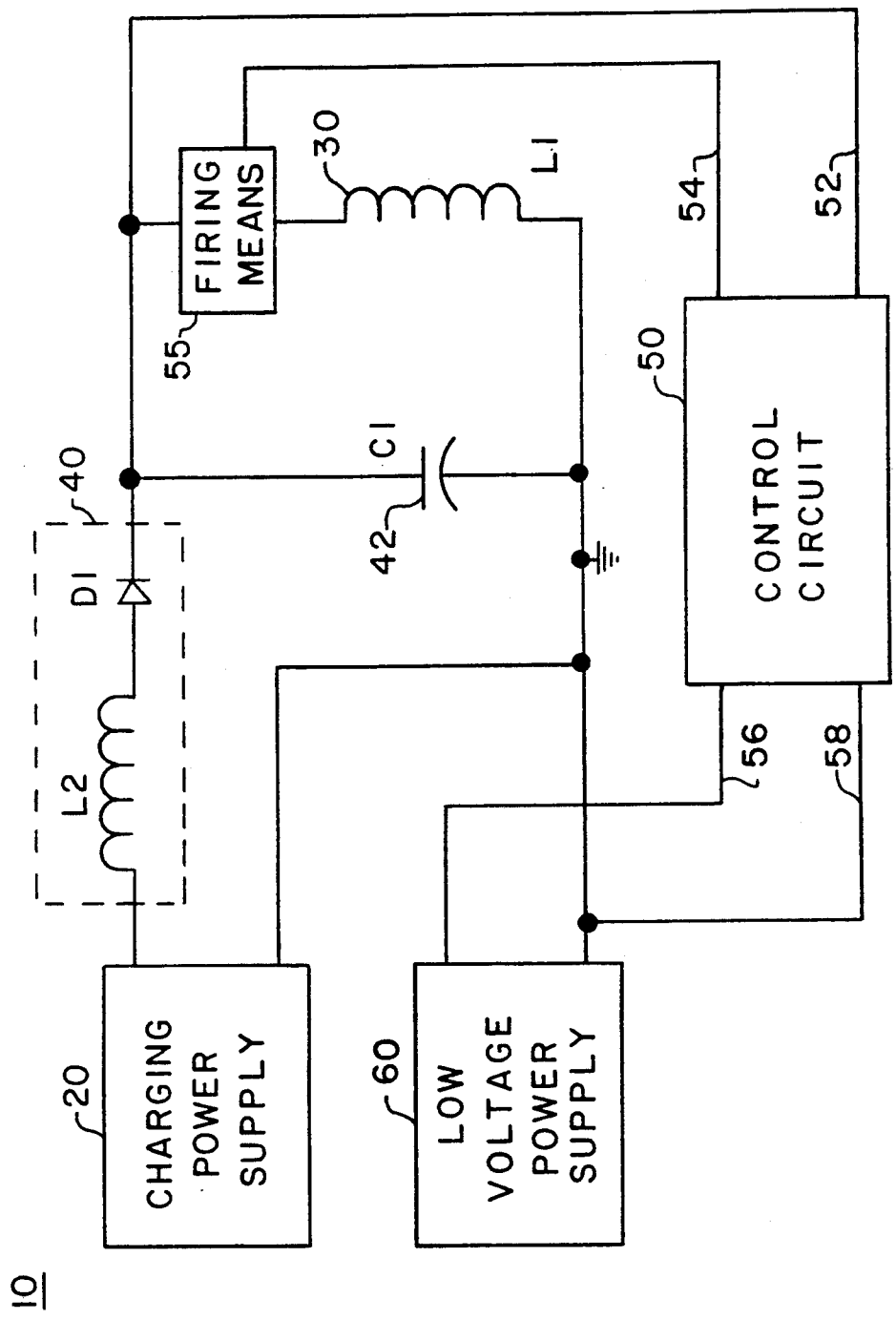
FIG. 1 is a simplified schematic of the present invention.

FIG. 1 depicts, in simplified form, a magnetic neural stimulator 10 comprising a charging power supply 20, a stimulation coil 30, a charging circuit 40, energy storage means 42, a control circuit 50, firing means 55 and a low voltage power supply 60.

Charging power supply 20 comprises a power supply to power charging circuit 40 and charge energy storage means 42. Power supply 20 maintains energy storage means 42 at least partially charged during sustained operation of the magnetic neural stimulator. Power supply 20 preferably is an adjustable power supply and may be powered by a conventional 120 VAC, 60 Hz, 15 amp household wall outlet supply. Alternatively, a 220 VAC supply may be employed. Desired operating characteristics such as magnetic pulse amplitude, duration and frequency generally dictate the power requirements and the output voltage setting for power supply 20.

Stimulation coil 30 comprises means such as inductor L1, for producing a magnetic field upon the application of current. Inductor L1 may be housed in a hand held probe (not shown).

Charging circuit 40 comprises serially connected inductor L2 and diode D1. The serial combination of inductor L2, diode D1 and energy storage means 42 which forms a resonant charging circuit is connected across charging power supply 20. Inductor L2 illustratively is a 5 mH high current inductor. Energy storage means 42 illustratively is implemented as a group or bank of capacitors connected in parallel and is schematically depicted as capacitor C1. For example, energy storage means 42 may comprise sixteen 20 μF, 1000 volts polypropylene capacitors wired in parallel. Diode D1 blocks the discharge of energy storage means 42 back into charging power supply 20.

Control circuit 50 and firing means 55 control the firing of stimulation coil 30 which forms a resonant discharging circuit with energy storage means 42. Control circuit 50 is provided with a capacitor voltage level input on line 52. Control circuit 50 preferably comprises a timing pulse generator and a transformer isolated driver or an optically isolated driver. Firing means 55 is preferably a silicon-controlled rectifier (SCR). Firing means 55 is controlled by a signal output by control circuit 50 on output line 54. The SCR permits current to flow in a forward direction under control of a trigger input; the SCR depicted does not permit reverse current flow, although reverse current flow may be permitted in other embodiments such as those which provide bipolar magnetic pulses. Low voltage power supply 60 provides power to control circuit 50 on lines 56, 58.

Magnetic neural stimulator 10 operates as follows. Initially, power for the stimulator is off and capacitor C1 is completely discharged. When the system power is turned on, charging power supply 20 supplies power to the stimulator. Current begins to flow through inductor L2 thereby charging capacitor C1. After some time (about 1 millisecond) the voltage on capacitor C1 reaches the output voltage of charging power supply 20, illustratively 100 volts. At this point, there is still substantial current through inductor L2. As a result, although the voltage across capacitor C1 is the same as that output by charging power supply 20, the current through inductor L2 continues to flow in the same direction thereby raising the voltage across capacitor C1 beyond that output by the power supply. More particularly, the energy stored in inductor L2 as current is discharged into capacitor C1 (which has previously been charged to 100 volts) until the voltage across capacitor C1 reaches about twice the output voltage of charging supply 20. The amount by which the voltage across C1 is increased depends, in part, on the amount of energy lost as heat during the charging of capacitor C1. Diode D1 blocks the discharge of capacitor C1 back into the charging power supply.

After the initial charging cycle is complete, the SCR can be triggered. When the SCR is triggered by control circuit 50, current flows from capacitor C1 into inductor L1 until all of the energy stored in capacitor C1 as voltage is transferred into energy stored in inductor L1 as current. At this point, the voltage across capacitor C1 is zero.

Again, the current in the inductor—in this case inductor L1—continues to flow in the same direction; and the energy stored as current in inductor L1 is transferred back into energy stored as a negative voltage across capacitor C1. Eventually, the current through inductor L1 reaches zero, at which point the voltage across capacitor C1 is about minus 180 volts. At this point, the SCR commutates and prevents the discharge of capacitor C1 back through inductor L1.

Meanwhile, starting at the time that the voltage across capacitor C1 fell below the output voltage of the charging power supply 20, current has resumed flowing through inductor L2. Now, however, since the voltage across capacitor C1 is about minus 180 volts, and since charging supply 20 is supplying 100 volts, there is about 280 volts across the combination of inductor L2 and diode D1. As will be appreciated, the increased voltage across the combination of inductor L2 and diode D1 produces a current through inductor L2 that charges capacitor C1 to a higher voltage, which can be shown to be approximately plus 380 volts.

This process is repeated every time the SCR is fired by the control circuit; and the voltage across capacitor C1 rises steadily toward a maximum value of approximately 600 volts.

The transfer of energy stored as charge in capacitor C1 into current through inductor L1 and back as charge in capacitor C1 generates the pulsed unipolar magnetic field that stimulates the tissue. Advantageously, the resonant charging circuit eliminates the need for a high voltage power supply and facilitates generation of magnetic pulses.

In an alternative embodiment, a diode is connected in parallel with SCR 55 of FIG. 1 to permit reverse current flow. The diode is connected with a polarity opposite to that of the SCR. Such a connection permits current to flow in a direction opposite from the current flow through SCR 55. As will be appreciated, this configuration permits a negative voltage across capacitor C1 to be discharged through the diode and inductor L1 thus producing a magnetic pulse of opposite polarity from that produced due to a discharge of a positive voltage across the capacitor into inductor L1. In this embodiment, successive magnetic pulses of alternating polarity are produced.

The inductance of inductor L2 is large, preferably at least on the order of ten times the inductance of inductor L1 and advantageously on the order of 50 times the inductance of inductor L1. The embodiment of FIG. 1 produces magnetic pulses of duration approximately 120 $\mu$sec.

The circuit of the present invention will operate suitably for a variety of values for inductors L1, L2 and capacitor C1. As will be appreciated, decreasing the inductance of inductor L2 will cause capacitor C1 to charge faster; decreasing the inductance of inductor L1 will cause the magnetic stimulation pulse to decrease in amplitude; and decreasing the capacitance of capacitor C1 will reduce the width of the stimulation pulse.

The rate of generation of stimulation pulses is limited by the energy lost to heat and the amount of power that can be obtained from the power supply to which the device is connected. Typical household power outlets supply 120 volts at a maximum current of 15 amps, providing 1800 watts of power. A stimulation rate of about 40 stimulations per second has been achieved with the embodiment of FIG. 1 and a 120 volt, 15 amp power supply.

Figure 2:
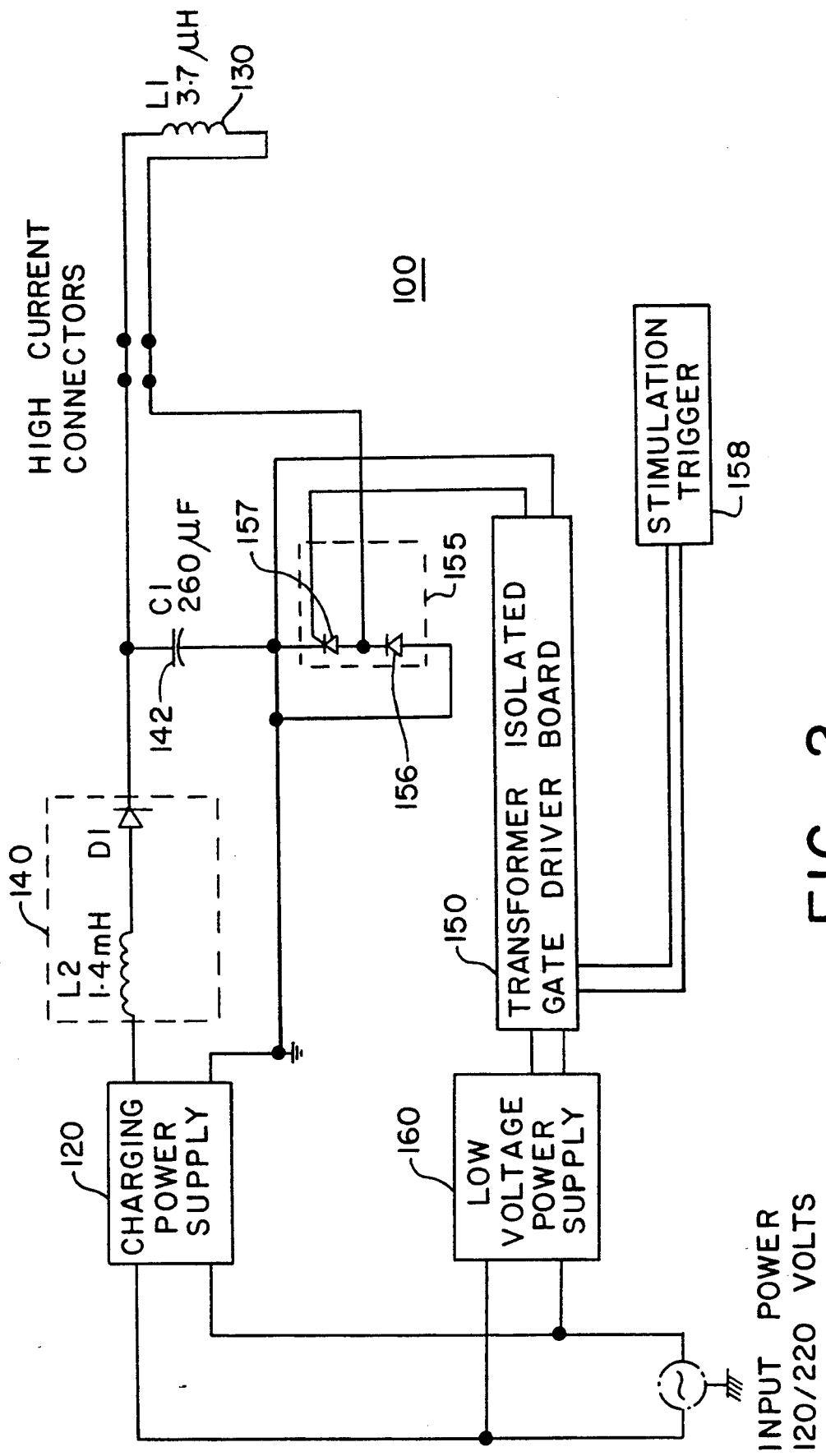
FIG. 2 is a schematic of an alternate embodiment of the present invention.

Referring now to FIG. 2, there is depicted a magnetic neural stimulator 100 capable of producing magnetic pulses of alternating polarity. Magnetic stimulator 100 comprises a charging power supply 120, a stimulation coil 130, a charging circuit 140, energy storage means 142, a gate driver board 150, firing means 155 and a low voltage power supply 160.

Charging power supply 120, stimulation coil 130, energy storage means 142, gate driver board 150 and low voltage power supply 160 are structurally and functionally similar to charging power supply 20, stimulation coil 30, energy storage means 42, control circuit 50 and low voltage power supply 60, respectively, of FIG. 1.

Broadly considered, charging circuit 140 and firing means 155 are similar to charging circuit 40 and firing means 55 of FIG. 1. Charging circuit 140 comprises serially connected inductor L2 and diode D!; and these elements and energy storage means 142 constitute a resonant charging circuit. Energy storage means 142 is in the form of a capacitor bank schematically depicted as capacitor C1. Illustratively, inductor L2 is a 1.4 mH inductor, capacitor C1 us a 260 $\mu$F capacitor bank and stimulation coil 130 includes a 3.7 $\mu$H inductor. Firing means 155 comprises diode means 156 and SCR means 157 and is adapted to provide magnetic pulses of alternating polarity. A stimulation trigger input 158 is also included to initiate firing of the stimulation coil.

Magnetic neural stimulator 100 operates as follows. Initially, power for the stimulator is off, capacitor C1 is completely discharged, and charging power supply 120 is illustratively set to generate an output of 100 volts. When the system power is turned on, charging power supply 120 provides 100 volts across charging circuit 140. Current begins to flow through inductor L2, thereby charging capacitor C1. After about 1 millisecond, capacitor C1 is charged to about 100 volts; and additional energy is stored in inductor L2 due to the current passing through it. The current in inductor L2 continues to flow in the same direction so that the energy stored in inductor L2 charges capacitor C1 to about 200 volts. Diode D1 prevents capacitor C1 from discharging back into charging power supply 120 by blocking the reverse current flow from capacitor C1. Since the voltage across capacitor C1 is now about twice that supplied by supply 120, this circuit acts as a voltage doubler.

At this point the system is ready to generate its first pulse of current. When the gate of SCR 157 is triggered by gate driver 150, it starts to conduct allowing capacitor C1 to discharge through the stimulation coil L1 creating a high current pulse. As in the case of the circuit of FIG. 1, capacitor C1 and inductor L1 form a resonant discharging circuit.

Current through inductor L1 continues to flow, establishing a negative voltage across capacitor C1; and eventually the current through inductor L1 reaches zero. After the energy transfer from inductor L1 back to capacitor C1 is complete, the voltage on capacitor C1 is about minus 180 volts. As a result there is about 280 volts present across inductor L2.

At this point, the voltage across capacitor C1 is a local maximum negative voltage and current starts flowing through inductor L1 in a reverse direction by way of diode 156. This reverse current through inductor L1 produces magnetic pulses of opposite polarity from that produced by forward current through inductor L1. The reverse current through inductor L1 flows until the voltage across capacitor C1 is zero, at which point one cycle is complete, i.e., a positive and a negative magnetic pulse have been produced.

Meanwhile, starting at the time that the voltage across capacitor C1 fell below the output voltage of the charging power supply 120, current has resumed flowing through inductor L2. This current continues flowing as the voltage drop across inductor L2 increases to about 280 volts. As in the case of the circuit of FIG. 1, this voltage drop produces a current through inductor L2 that produces a still greater positive voltage of about 380 volts due to increased current flow through inductor L2.

Figure 3:
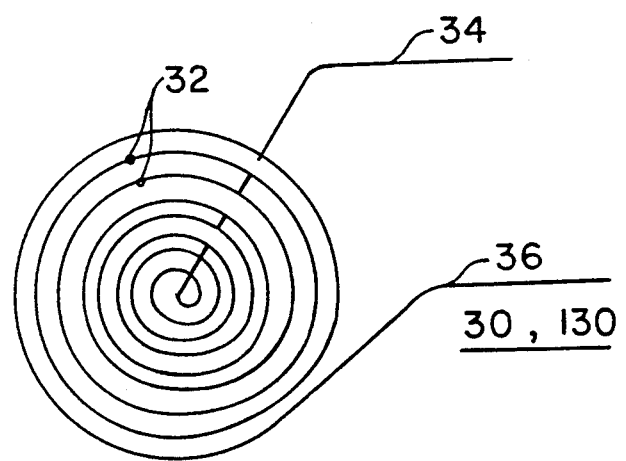
FIG. 3 is a schematic of the stimulation coil depicted in FIGS. 1 and 2.

FIG. 3 schematically depicts a stimulation coil suitable for use with the circuit depicted in FIG. 1 as well as FIG. 2. The stimulation coil comprises conductor 32 wound in a helical manner and having conducting leads 34, 36.

More specifically, in one embodiment the stimulation coil includes a flat wound wire coil with conductor 32 in the form of insulated flat wire windings wound as far to the center of the coil as practically possible. A cross-section of the wire is approximately rectangular measuring approximately ¾ cm by 1 mm. The flat wire is coiled about itself to produce a disk-shaped coil having a diameter of about 2 cm and a thickness of about ¾ cm. Magnetic material is preferably provided adjacent the disk-shaped wire coil, as will be described in conjunction with FIG. 7. Advantageously, this geometry produces a stronger magnetic field near the center of the coil than conventional toroidal coils. Alternatively, a flat wound wire coil which is wound around a magnetic material may be employed. Illustratively, such a flat wound wire coil has a diameter on the order of 4½ inches. The magnetic material increases the strength of the magnetic field generated for a given input of current. The direction of the magnetic field is given by the so-called right hand rule. For example, if the current flows clockwise in the embodiment of FIG. 3, the magnetic field B is directed into the page upon which FIG. 3 is printed.

In an alternative embodiment, the coil is water cooled and the conductors in the coil may be formed from copper tubing containing the cooling medium, i.e., water. Such copper tubing is illustratively ¼ inch in diameter and is insulated by a plastic coating. Alternatively, water may be passed sufficiently close to the wire wound embodiment to adequately remove heat. Water cooling allows increased dissipation of power in the stimulation coil and yet maintains an acceptable temperature in the coil.

Figure 4:
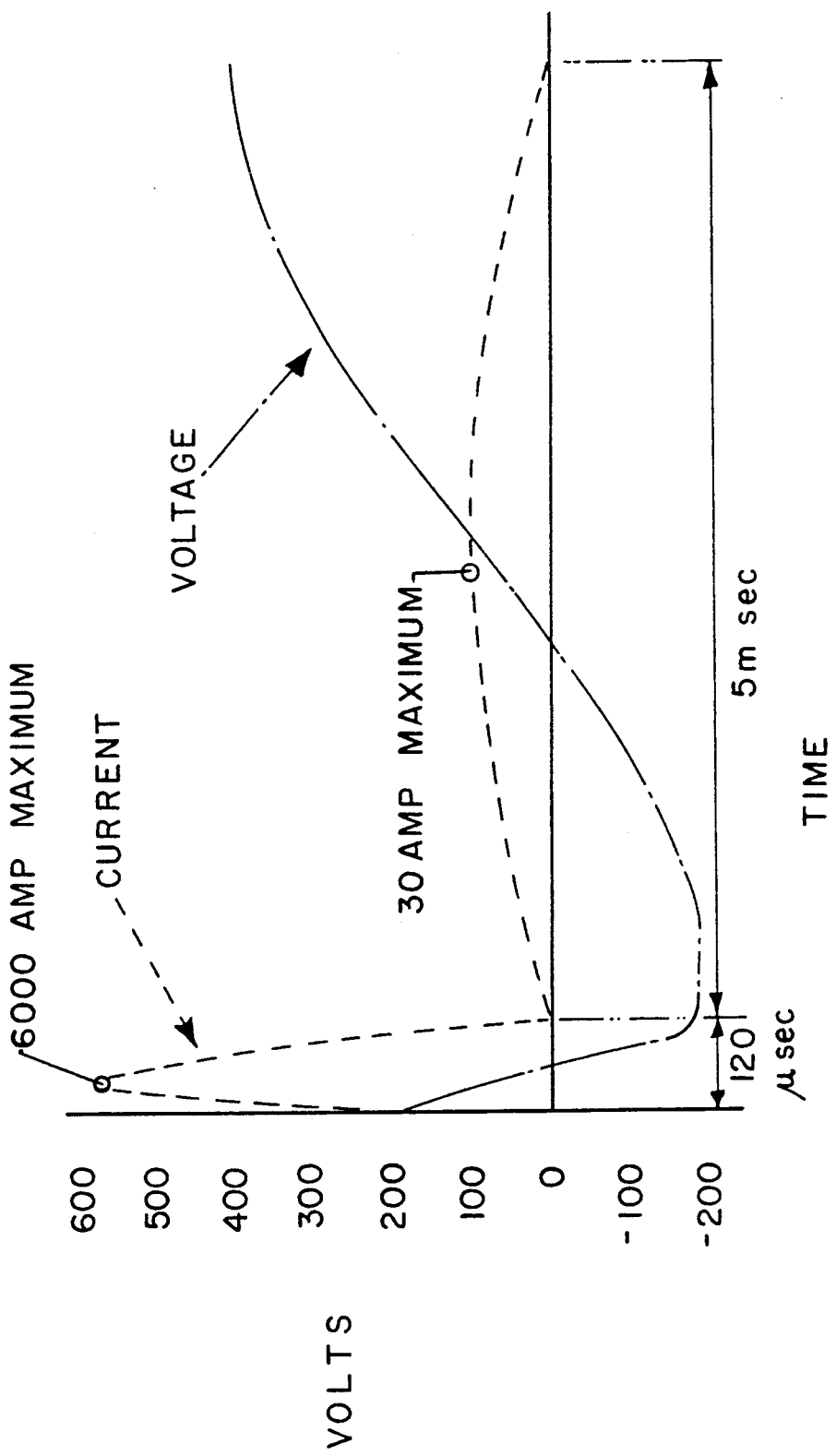
FIG. 4 is a graph depicting voltage and current characteristics versus time of the energy storage capacitor C1 of FIG. 2 for a single current pulse.

FIG. 4, which is not drawn to scale, depicts the voltage across capacitor C1 versus time for the embodiment of FIG. 2 from the moment the SCR is triggered. As is apparent, the voltage across capacitor C1 decreases from 200 volts to −180 volts during the first 120 μsec. of operation after triggering of the SCR. This voltage then increases from −180 volts to about 600 volts during the remainder of this charge/discharge cycle. FIG. 4 also schematically depicts the current through capacitor C1 versus time. Thus, it is seen that the maximum current is about 6,000 amps.

Figure 5:
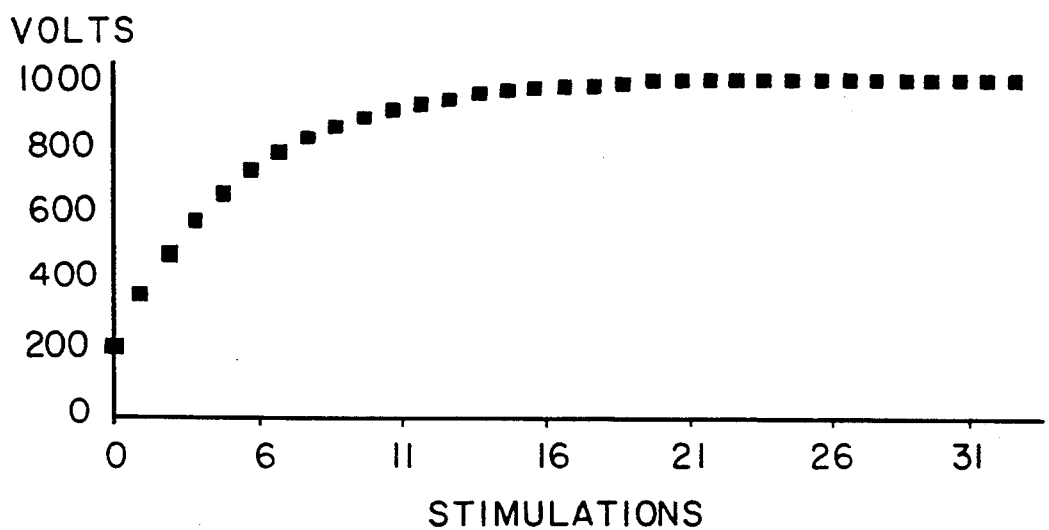
FIG. 5 is a graph depicting voltage characteristics versus the number of stimulations for the energy storage capacitor C1 of FIG. 2.

FIG. 5 depicts the voltage across capacitor C1 as a function of the number of stimulations for the embodiment of FIG. 2. As will be appreciated, the voltage across capacitor C1 reaches a maximum, steady-state, value of about 1,000 volts after about twenty-five discharges.

As in the embodiment of FIG. 1, the output of the charging supply voltage 120 (FIG. 2) may be adjusted to generate the stimulation level desired. The peak positive voltage on capacitor C1 can be determined from the following equation:

$$V_{peak} = \frac{V_{in}}{1 - E_{ff}} \quad (10)$$

where

Vin = the output voltage of the charging power supply
Vpeak = the peak voltage across capacitor C1 and
Eff = the efficiency of the energy transfers.

Figure 6:
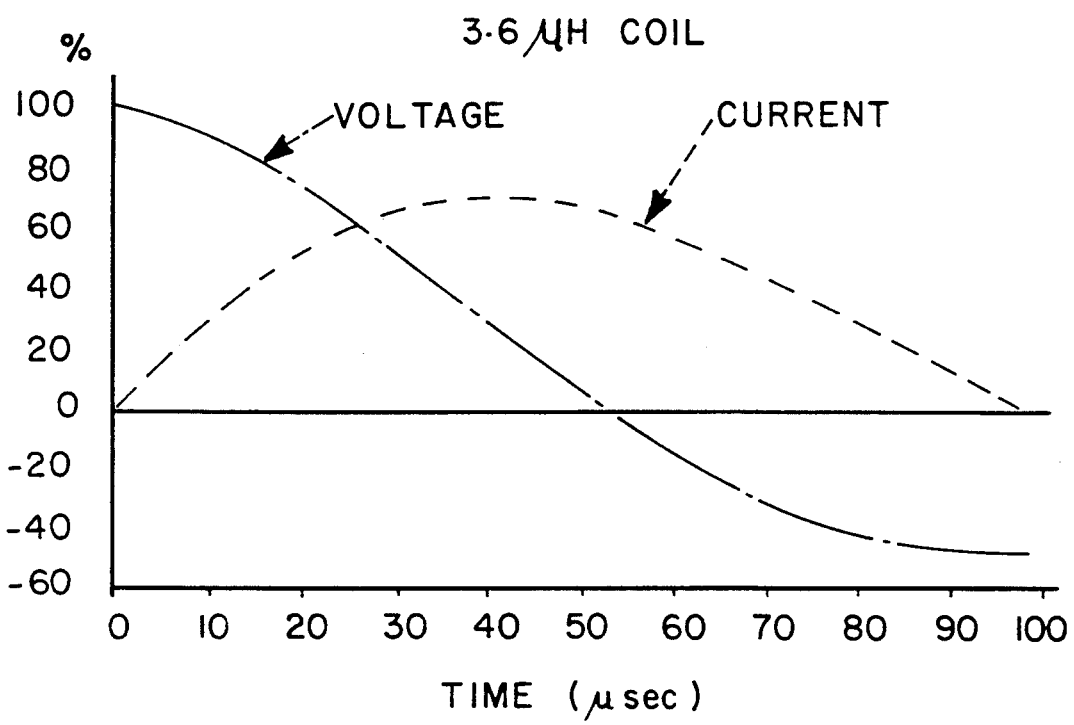
FIG. 6 is a graph depicting voltage and current characteristics versus time of the stimulation coil for a single current pulse during steady-state operation.

FIG. 6 depicts the voltage across and current through the 3.6 μH inductor of the stimulation coil versus time for the positive half of a current pulse once steadystate operation has been achieved, for the embodiment of FIG. 2.

Figure 7:
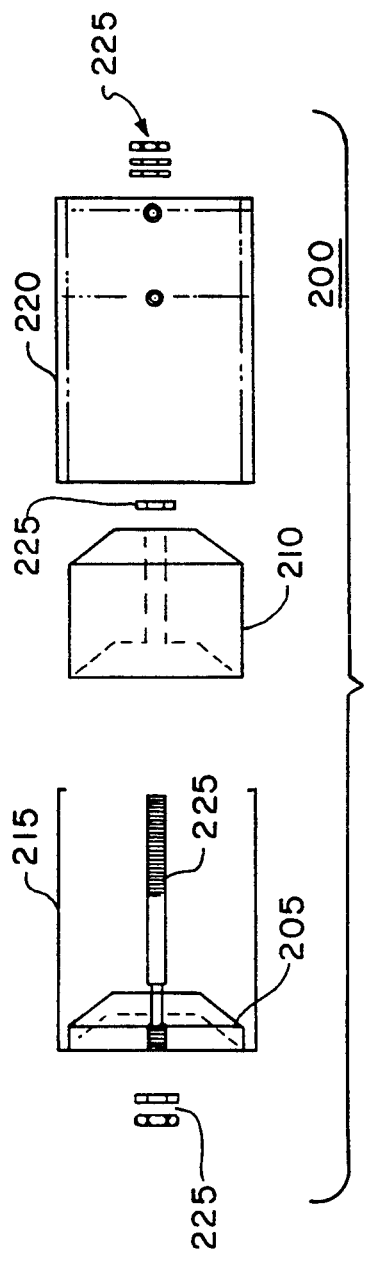
FIG. 7 depicts a stimulation coil suitable for use with the present invention.

FIG. 7 depicts a stimulation probe 200 suitable for use with the present invention comprising a disk-shaped wire winding 205, a magnetic material 210, an inner housing 215, an outer housing 220 and retaining means 225. Retaining means 225 is depicted as a nut and bolt assembly which firmly fastens winding 205, material 210 and housings 215, 220 together. Advantageously, magnetic material 210 serves to suitably shape the magnetic pulse which emanates from wire winding 205 upon the application of power to the winding. Wire winding 205 illustratively has a diameter on the order of 2 cm. Permalloy has been found suitable for use as magnetic material 210.

Figure 8:
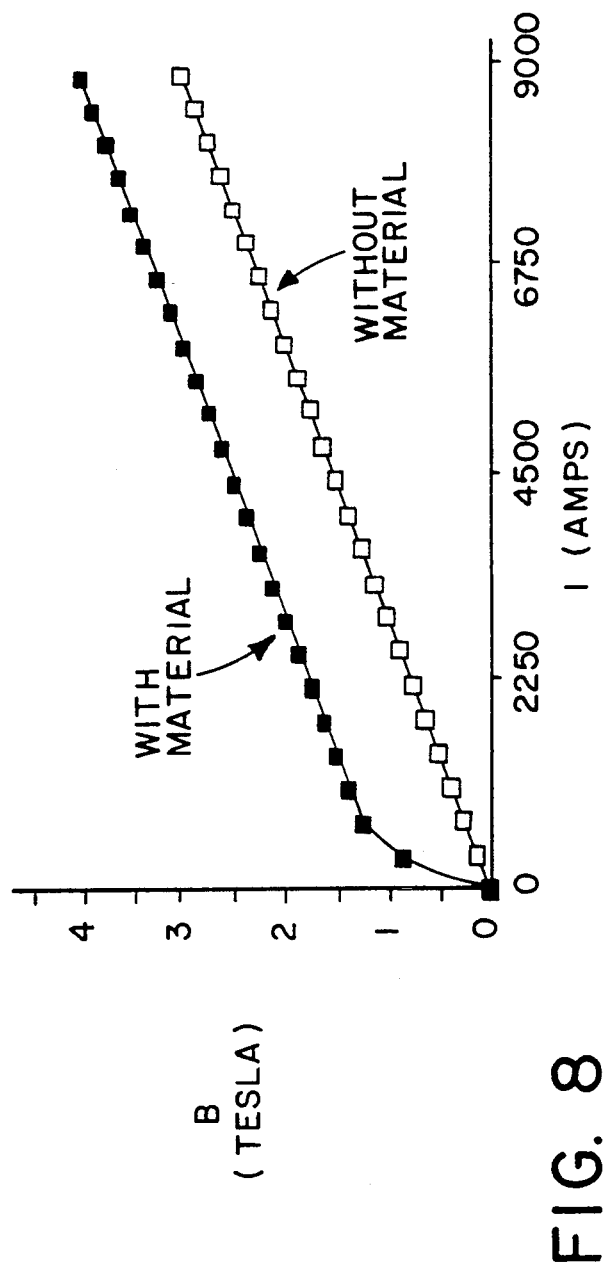
FIG. 8 is a graph depicting the strength of the magnetic field versus applied current for the stimulation coil of FIG. 7.

FIG. 8 quantitatively depicts the benefit gained by use of pulse-shaping magnetic material 210. In particular, FIG. 8 depicts the magnetic field B (Tesla) versus applied current (amps) for an illustrative stimulation coil such as the type depicted in FIG. 7 with and without the magnetic material.

Figure 9:
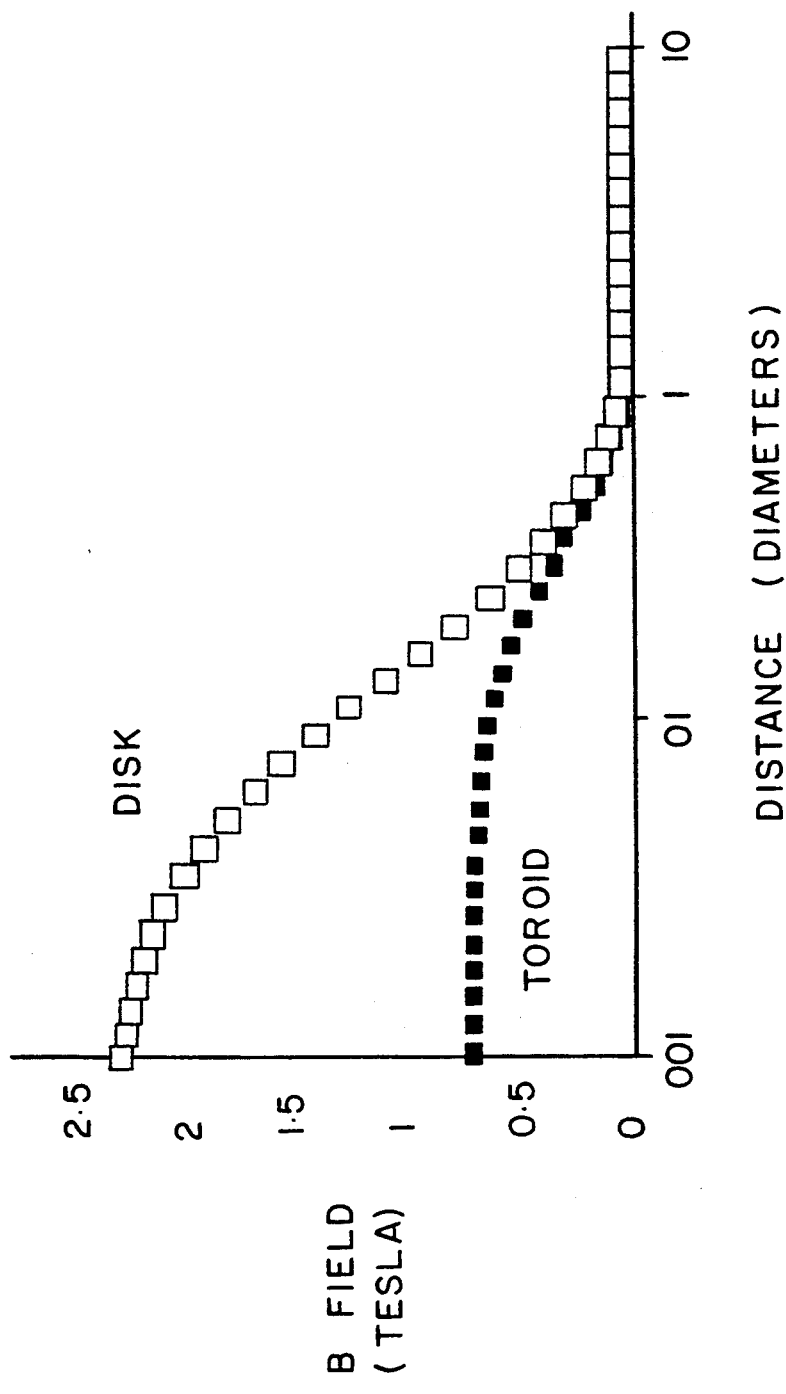
FIG. 9 is a graph depicting the magnetic field strength versus penetration depth of a disk-shaped coil and a toroidal coil.

FIG. 9 depicts the penetration depth (in diameters of disk-shaped wire winding) versus the magnetic field produced at that depth for the present disk-shaped winding and also for conventional toroidal shaped windings. As is apparent, the disk-shaped winding offers greater magnetic field strength, especially for decreased penetration depths.

Assuming a 20% energy loss per stimulation, a standard household power supply of 120 volts, 15 amps can theoretically sustain a stimulation rate of about 70 stimulations per second. Analogously, a 220 volt, 20 amp supply should sustain a rate of about 400 stimulations per second.

Of the 20% energy loss per stimulation, a small amount is deposited into the subject. A majority of the 20% loss appears as heat in the coil. Accordingly, the maximum practical stimulation rate for an air cooled stimulation coil is about 5 stimulations per second. However, use of water cooling eliminates the stimulation coil heating problem and 70 stimulations per second may indeed by achieved with a 120 volt, 15 amp supply.

Thus, it can be seen that there is provided a high speed magnetic neural stimulator capable of selectively stimulating small regions of biological tissue. A resonant charging circuit is employed to permit the generation of the high frequency magnetic pulses.

It is to be understood that the invention can be carried out by specifically different equipment and devices and that various modifications, both as to equipment details and operating procedures can be effected without departing from the spirit and scope of the claimed invention.

For example, each of the individual magnetic pulses (typically of 120 μsec. duration for the embodiments in FIGS. 1 and 2) emanating from the stimulator may be replaced with a rapid series of closely spaced pulses of short duration. The power required to produce such a rapid series of brief pulses is less than that required for a single longer pulse since such a single longer pulse requires maintaining a high power requirement. With a rapid series of brief pulses, the magnetic field may return to zero between pulses, and it is not required to maintain the high peak magnetic field. Thus, by stimulating with a rapid series of brief (on the order of 100 ns to 10 μsec) high dB/dt pulses, rather than a single longer pulse, it may be possible to significantly reduce both the power requirement and probe heating. Furthermore, the rapid series of brief pulses may be modulated to produce an envelope with a desired shape.

Further, a dedicated microprocessor may be provided to monitor various voltage and current levels as well as component status and to shut down the stimulator should a malfunction occur. Additionally, the microprocessor can control the firing of the firing means. As will be appreciated by one skilled in the art, by controlling the firing of the firing means, unipolar magnetic pulses as well as magnetic pulses of alternating polarity may be produced.

What is claimed is:

1. A magnetic neural stimulator for stimulating biological tissue comprising:
    (a) magnetic stimulating means for producing a magnetic field,
    (b) energy storage means for storing electromagnetic energy,
    (c) firing means for gating stored energy from said energy storage means to said magnetic stimulating means thereby producing a magnetic pulse,
    (d) control circuit means for supplying a firing signal to said firing means thereby causing said firing means to gate stored energy from said energy storage means to said magnetic stimulating means and producing said magnetic pulse, and
    (e) charging circuit means for repetitively charging said energy storage means, said circuit means charging said energy storage means to a peak voltage level which is greater than the peak voltage level of a power supply which powers said charging circuit means,
    wherein each charging of said energy storage means by said charging circuit means is followed by gating at least a portion of energy stored in said energy storage means to said magnetic stimulating means, and wherein an inductance value of an inductor of said charging circuit means is at least ten times an inductance value of said magnetic stimulating means.

2. The magnetic neural stimulator of claim 1 wherein the inductance value of said inductor of said charging circuit means is on the order of fifty times the inductance value of said stimulating means.

3. A magnetic neural stimulator for stimulating biological tissue comprising:
    (a) magnetic stimulating means for producing a magnetic field,
    (b) energy storage means for storing electromagnetic energy,
    (c) a linear amplifier for gating stored energy from said energy storage means to said magnetic stimulating means thereby producing a magnetic pulse,
    (d) control circuit means for supplying a firing signal to said linear amplifier thereby causing said linear amplifier to gate stored energy from said energy storage means to said magnetic stimulating means and for producing said magnetic pulse, and
    (e) a charging circuit for repetitively charging said energy storage means,
    wherein each charging of said energy storage means by said charging circuit is followed by gating a portion of energy stored in said energy storage means to said magnetic stimulating means.

4. A magnetic neural stimulator for stimulating biological tissue comprising:
    (a) magnetic stimulating means for producing a magnetic field,
    (b) energy storage means for storing electromagnetic energy,
    (c) a plasma switch for gating stored energy from said energy storage means to said magnetic stimulating means thereby producing a magnetic pulse,
    (d) control circuit means for supplying a firing signal to said plasma switch thereby causing said plasma switch to gate stored energy from said energy storage means to said magnetic stimulating means and for producing said magnetic pulse, and
    (e) A charging circuit for repetitively charging said energy storage means,
    wherein each charging of said energy storage means by said charging circuit is followed by gating a portion of energy stored in said energy storage means to said magnetic stimulating means.

5. A magnetic neural stimulator for stimulating biological tissue comprising:
    (a) a coil of conductive tubing for producing a magnetic field, said coil adapted to be cooled by a fluid flowing through said tubing,
    (b) energy storage means for storing electromagnetic energy,
    (c) firing means for gating stored energy from said energy storage means to said coil thereby producing a magnetic pulse,
    (d) control circuit means for supplying a firing signal to said firing means thereby causing said firing means to gate stored energy from said energy storage means to said coil and producing said magnetic pulse, and
    (e) charging circuit means for repetitively charging said energy storage means, said circuit means charging said energy storage means to a peak voltage level which is greater than the peak voltage level of a power supply which powers said charging circuit means,
    wherein each charging of said energy storage means by said charging circuit means is followed by gating at least a portion of energy stored in said energy storage means to said coil.

6. In a magnetic neural stimulator of the type having a wire winding for producing magnetic pulses, a capacitor for storing energy from a power supply and a circuit for supplying the stored energy to the wire winding, the improvement comprising a charging circuit having a serially connected inductor and diode cooperating with said capacitor for repetitively charging said capacitor wherein each charging of said capacitor is followed by a partial discharging of said capacitor into said wire winding, said charging circuit charging said energy storage means to a peak voltage level which is greater than the peak voltage level of a power supply which powers said charging circuit means, and said inductor having an inductance which is at least ten times the inductance of said wire winding.

7. A magnetic neural stimulator for stimulating biological tissue comprising:
    (a) a coil of conductive tubing for producing a magnetic field, said coil adapted to be cooled by a fluid flowing through said tubing,
    (b) energy storage means for storing electromagnetic energy,
    (c) firing means for gating stored energy from said energy storage means to said coil thereby producing a magnetic pulse,
    (d) control circuit means for supplying a firing signal to said firing means thereby causing said firing means to gate at least a portion of stored energy from said energy storage means to said coil and producing said magnetic pulse, part of said portion of stored energy gated to said coil returning to said energy storage means, and (e) charging circuit means for repetitively charging said energy storage means, wherein each charging of said energy storage means by said charging circuit means is followed by gating said portion of energy stored in said energy storage means to said coil.

8. In a magnetic neural stimulator of the type having a wire winding for producing magnetic pulses, a capacitor for storing energy from a power supply and a circuit for supplying the stored energy to the wire winding, the improvement comprising a charging circuit having a serially connected inductor and diode cooperating with said capacitor for repetitively charging said capacitor wherein each charging of said capacitor is followed by a discharging of said capacitor into said wire winding, said discharging being followed by a transfer of a portion of energy discharged into said wire winding back into said capacitor, and said inductor having an inductance which is at least ten times the inductance of said wire winding, and wherein a peak voltage level is provided across said capacitor which is greater than the peak voltage level of a power supply which powers said charging circuit.

* * * * *

UNITED STATES PATENT AND TRADEMARK OFFICE
CERTIFICATE OF CORRECTION

PATENT NO. : 5,061,234
DATED : 10-29-91
INVENTOR(S) : Richard A. Chaney

It is certified that error appears in the above-indentified patent and that said Letters Patent is hereby corrected as shown below:

Please insert the following paragraph in column 1, line 4 after the title:

--This invention was made with government support under contract awarded by the National Institute of Health. The government has certain rights to the invention.--

Signed and Sealed this

Eleventh Day of October, 1994

Attest:

BRUCE LEHMAN

Attesting Officer

Commissioner of Patents and Trademarks